United States Patent [19]

Nakajima et al.

[11] Patent Number: 5,530,001
[45] Date of Patent: Jun. 25, 1996

[54] PHARMACEUTICAL USE OF DIHYDROPYRIDINE DERIVATIVE

[75] Inventors: Masahide Nakajima; Norifumi Nakamura; Feng Wang; Koichi Yamanouchi; Kazutaka Hayashi; Hideaki Kido; Yoshiji Kubo; Minori Okita; Takeshi Uchida; Masahiro Watanabe; Katsumi Yamanaga; Hiroshi Shinyama; Toru Kawamura; Yuji Narita, all of Hirakata, Japan

[73] Assignee: The Green Cross Corporation, Osaka, Japan

[21] Appl. No.: 360,705

[22] PCT Filed: Mar. 22, 1994

[86] PCT No.: PCT/JP94/00460

§ 371 Date: Feb. 24, 1995

§ 102(e) Date: Feb. 24, 1995

[87] PCT Pub. No.: WO94/23721

PCT Pub. Date: Oct. 27, 1994

[30] Foreign Application Priority Data

Apr. 19, 1993 [JP] Japan .................... 5-091635
Jun. 8, 1993 [JP] Japan .................... 5-137636

[51] Int. Cl.$^6$ ................... A61K 31/495; A61K 31/44
[52] U.S. Cl. ................... 514/255; 514/334; 514/356; 514/824; 514/870; 514/925; 514/929
[58] Field of Search ................... 514/255, 334, 514/356, 824, 870, 925, 929

[56] References Cited

U.S. PATENT DOCUMENTS 4,886,819 12/1989 Ashimori et al. ................... 514/356

OTHER PUBLICATIONS

J. Cardiovasc. Pharmacol, vol. 17, No. 4, 1991 pp. 546–550, H. Sinzinger et al. "Isradipine, a Calcium–Entry Blocker, Decreases Vascular (125I) LDL Entry in Hypercholesteremic Rats".

Biomed. Biochim. ACTA., vol. 47, No. 11–11, 1988 pp. S324–S327, G. N. Baldenkov et al. "Prostacyclin, Thromboxane A2 and Calcium Antagonists: Effects on Atherosclerotic Characteristics of Vascular Cells".

*Primary Examiner*—Kimberly Jordan
*Attorney, Agent, or Firm*—Sughrue, Mion, Zinn, Macpeak & Seas

[57] ABSTRACT

A novel pharmaceutical use of a dihydropyridine derivative of the formula (I)

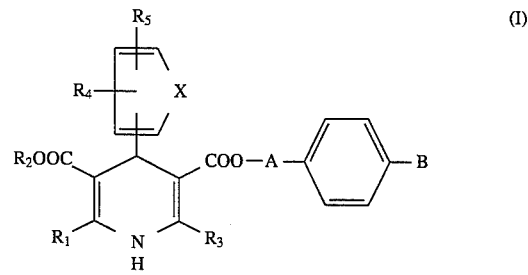

wherein $R_1$, $R_2$ and $R_3$ are the same or different and each is an alkyl or the like; $R_4$ is a hydrogen atom or the like; $R_5$ is nitro, a halogenated alkyl, cyano or the like; X is a vinylene or an azomethine; A is an alkylene; and B is —$N(R_6)(R_7)$ or a group of the formula

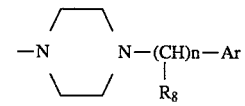

wherein $R_6$ and $R_7$ are the same or different and each is an alkyl, an aralkyl, an aryl or the like; $R_8$ and Ar are aryl or the like; and n is 0, 1 or 2, or an acid addition salt thereof for promoting $PGI_2$ production, and for the treatment and prevention of hyperlipemia, arteriosclerosis and cerebral diseases.

6 Claims, No Drawings

PHARMACEUTICAL USE OF DIHYDROPYRIDINE DERIVATIVE

This application is a 371 of PCT/JP94/00460 filed Mar. 22, 1994.

TECHNICAL FIELD

The present invention relates to a novel pharmaceutical use of dihydropyridine derivatives having a specific structure to be shown below. More particularly, the present invention relates to a novel pharmaceutical use of dihydropyridine derivatives for promoting $PGI_2$ production, and for the prevention and treatment of hyperlipemia, arteriosclerosis and cerebral diseases.

BACKGROUND ART $PGI_2$ (prostacyclin) is one of the substances synthesized by arachidonic acid cascade and is confirmed to have many physiological actions such as a platelet coagulation-suppressive action, a smooth muscle relaxing action, a gastric acid secretion-suppressive action, a tunica mucosa ventriculi-protective action, an organ blood flow-increasing action and a tumor metastasis-suppressive action.

$PGI_2$ synthase is present, particularly in large amounts, in vascular endothelial cells and vascular smooth muscle cells, and various production-stimulating substances promote production of $PGI_2$.

From the studies heretofore done with regard to $PGI_2$, it is known that substances such as arachidonic acid, bradykinin, histamine, serotonin, thrombin, calcium ionophore A23187, $\alpha$-toxin, leukotriene $C_4$ and $D_4$, PDGF (platelet derived growth factor), HDL-cholesterol, human serum, nitroglycerin, angiotensin I and II and vitamin C have $PGI_2$ production-stimulating action. The substances which promote $PGI_2$ production are expected to become drugs useful for the diseases, for which the actions of $PGI_2$, such as vasodilating action, bronchodilating action, gastric acid secretion-suppressive action and tumor metastasis-suppressive action, give the desired effects for improvement.

Hyperlipemia, arterioscrelosis and cerebral diseases (e.g., cerebral stroke, cerebral edema, cerebral softening, cerebral hemorrhage and cerebral infarction) are typical adult diseases on the rise in recent years along with the aging society, and the development of a pharmaceutical agent effective for the prevention and treatment of these diseases is desired.

Hyperlipemia is a condition accompanied by an abnormal increase in serum lipids, such as cholesterol, triglyceride and phospholipid. These lipids form, together with apoprotein, a macromolecular complex called lipoprotein in plasma. A lipoprotein is classified into five fractions of chylomicron, very low density lipoprotein (VLDL), low density lipoprotein (LDL), intermediate density lipoprotein (IDL) and high density lipoprotein (HDL), according to the degree of density. Hyperlipemia is, for the convenience's sake, classified into the expression types of I-type (increase in chylomicron), IIa-type (increase in LDL), IIb-type (increase in LDL and VLDL), III-type (increase in B-VLDL), IV-type (increase in VLDL) and V-type (increase in chylomicron and VLDL), according to the kind of lipoprotein that has increased in the serum.

From clinical and practical points of view, it is considered beneficial to deal with hyperlipemia by subdividing the disease into hypercholesterolemia and hypertriglyceridemia. The fundamental treatment for the both diseases is alimentary therapy and appropriate exercises. When the symptom is not improved, drug therapy is introduced. The therapeutic agents currently in use for hyperlipemia are anion exchange resin, cholesterol synthesis inhibitor (HMG-CoA reductase inhibitor) and probucol for hypercholesterolemia; and clofibrate preparations and nicotinic acid preparations for hypertriglyceridemia.

Arteriosclerosis is a local disease caused by thickening or hardening of artery wall and triggered by hypertension, hyperlipemia and diabetes. About 15% of the adults in our country are considered to have hypercholesterolemia and there are many patients suffering from arteriosclerosis caused by hypercholesterolemia.

The dihydropyridine derivative (I) to be mentioned later has a calcium channel antagonistic action and is useful as a hypotenser, a periphery and cerebral vasodilator and a therapeutic agent for coronary artery disorders (therapeutic agent for angina pectoris) (Japanese Patent Unexamined Publication No. 225356/1988, U.S. Pat. No. 4,886,819, EP-A- 257616).

The present inventors have conducted a wide variety of studies with regard to the dihydropyridine derivative (I) and found that said compound is extremely useful as a cerebral blood flow-increasing agent (Japanese Patent Unexamined Publication No. 62824/1990, EP-A-342577), a therapeutic agent for vasospasm (Japanese Patent Unexamined Publication No. 180826/1990, EP-A- 379737) and a heart stimulant (Japanese Patent Unexamined Publication No. 235168/1992, EP-A-463407).

DISCLOSURE OF THE INVENTION

The present inventors have found this time that the dihydropyridine derivative (I) and acid addition salts thereof have an unexpected action, which is different from the above-mentioned actions so far confirmed, namely, an action of promoting $PGI_2$ production in vascular endothelial cells, and that they are useful as $PGI_2$ production promoters.

In addition, the present inventors have found that the dihydropyridine derivative (I) and acid addition salts thereof have an action of suppressing increase of lipids in blood and that they are useful as agents for the prevention and treatment of hyperlipemia and arteriosclerosis.

The present inventors have further found that the dihydropyridine derivative (I) and acid addition salts thereof have notable action as agents for the prevention and/or treatment of cerebral diseases, as compared with benidipine, nicardipine and hydralazine.

Accordingly, the present invention aims at providing a novel pharmaceutical use of the dihydropyridine derivative (I).

More particularly, the present invention aims at providing a use of the dihydropyridine derivative (I) for promoting $PGI_2$ production.

The present invention further aims at providing a use of the dihydropyridine derivative (I) for the prevention and treatment of hyperlipemia and arteriosclerosis.

Moreover, the present invention aims at providing a use of the dihydropyridine derivative (I) for the prevention and treatment of cerebral diseases.

The present invention is as follows:
(1) A pharmaceutical agent for promoting $PGI_2$ production, comprising, as an active ingredient, a dihydropyridine derivative of the formula:

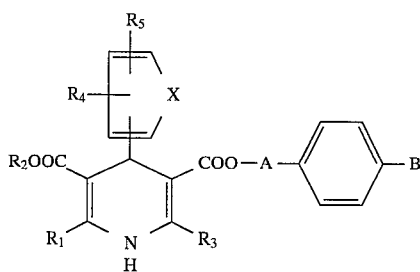

(I)

wherein $R_1$, $R_2$ and $R_3$ are the same or different and each is an alkyl, a cycloalkyl or an alkoxyalkyl;

$R_4$ and $R_5$ are the same or different and each is a hydrogen atom, a halogen, nitro, a halogenated alkyl, an alkylsulfonyl, a halogenated alkoxy, an alkylsulfinyl, an alkyl, a cycloalkyl, an alkoxy, cyano, an alkoxycarbonyl or an alkylthio, provided that $R_4$ and $R_5$ are not hydrogen atoms at the same time;

X is a vinylene or an azomethine;

A is an alkylene; and

B is $-N(R_6)(R_7)$ or a group of the formula

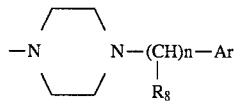

wherein $R_6$, $R_7$ and $R_8$ are the same or different and each is a hydrogen atom, an alkyl, a cycloalkyl, an aralkyl, an aryl or a pyridyl, Ar is an aryl or a pyridyl and n is an integer of 0, 1 or 2 [hereinafter referred to as dihydropyridine derivative (I)] or an acid addition salt thereof (generally a pharmacologically acceptable acid addition salt); a method for promoting $PGI_2$ production, comprising administering an effective amount of said compound; and a use of said compound for manufacturing a pharmaceutical agent for promoting $PGI_2$ production.

(2) A pharmaceutical agent for the prevention and treatment of hyperlipemia, comprising a dihydropyridine derivative (I) or an acid addition salt thereof as an active ingredient; a method for preventing and treating hyperlipemia, comprising administering an effective amount of said compound; and a use of said compound for manufacturing a pharmaceutical agent for preventing and treating hyperlipemia.

(3) A pharmaceutical agent for the prevention and treatment of arteriosclerosis, comprising a dihydropyridine derivative (I) or an acid addition salt thereof as an active ingredient; a method for preventing and treating arteriosclerosis, comprising administering an effective amount of said compound; and a use of said compound for manufacturing a pharmaceutical agent for preventing and treating arteriosclerosis.

(4) A pharmaceutical agent for the prevention and treatment of cerebral diseases, comprising a dihydropyridine derivative (I) or an acid addition salt thereof as an active ingredient; a method for preventing and treating cerebral diseases, comprising administering an effective amount of said compound; and a use of said compound for manufacturing a pharmaceutical agent for preventing and treating cerebral diseases.

Of the above, a compound, wherein $R_1$, $R_2$ and $R_3$ are the same or different and each is an alkyl, $R_4$ is a hydrogen atom, $R_5$ is nitro, a halogenated alkyl or cyano, $R_6$ and $R_7$ are the same or different and each is an alkyl, an aralkyl or an aryl, $R_8$ is an aryl, Ar is an aryl and n is 1, is particularly preferable.

The dihydropyridine derivative (I) and an acid addition salt thereof to be used in the present invention are extremely low toxic and show slow onset of long-lasting actions. Accordingly, they are highly effective and highly safe.

The symbols used in the present specification are explained in the following.

The alkyl represented by $R_1$, $R_2$ and $R_3$ may be straight or branched and is preferably a lower alkyl having 1 to 6 carbon atoms, which is exemplified by methyl, ethyl, propyl, isopropyl, butyl, isobutyl, sec-butyl, t-butyl, pentyl, isopentyl, neopentyl and hexyl, with preference given to those having 1 to 4 carbon atoms. The alkyl may have a lower cycloalkylalkyl having 3 to 6 carbon atoms on the alkyl terminal, such as cyclopropylmethyl, cyclobutylethyl and cyclopentylmethyl.

As the cycloalkyl represented by $R_1$, $R_2$ and $R_3$, preferred are lower cycloalkyls having 3 to 6 carbon atoms, such as cyclopropyl, cyclobutyl, cyclopentyl and cyclohexyl.

As the alkoxyalkyl represented by $R_1$, $R_2$ and $R_3$, preferred are those having 3 to 7 carbon atoms, such as methoxyethyl, ethoxyethyl, propoxyethyl, isopropoxyethyl, butoxyethyl, methoxypropyl, 2-methoxy-1-methylethyl and 2-ethoxy-1-methylethyl.

The substituent represented by $R_4$ and $R_5$ may be the same or different, and may bind to any position of the ring, with preference given to the 2- and/or 3-position relative to the binding site with the dihydropyridine ring.

As the halogen at $R_4$ and $R_5$, exemplified are fluorine atom, chlorine atom, bromine atom and iodine atom, and particularly preferred are fluorine atom and chlorine atom.

As the alkyl and the cycloalkyl, preferred are those mentioned for $R_1$ to $R_3$.

The alkoxy represented by $R_4$ and $R_5$ is preferably a lower alkyl having 1 to 3 carbon atoms, and exemplified by methoxy, ethoxy, propoxy and isopropoxy.

The alkylthio represented by $R_4$ and $R_5$ is preferably a lower alkyl having 1 to 3 carbon atoms, and exemplified by methylthio, ethylthio, propylthio and isopropylthio.

As the alkoxycarbonyl represented by $R_4$ and $R_5$, preferred are those having 2 to 4 carbon atoms, such as methoxycarbonyl, ethoxycarbonyl and propoxycarbonylo Halogen of the halogenated compound is exemplified by those mentioned above, and the halogenated alkyl may be that wherein some of the hydrogen atoms are replaced with halogen atoms [e.g., $(CF_3)_2CHCH_2-$ and $CF_3CH_2-$] or all of the hydrogen atoms are replaced with halogen atoms, such as trifluoromethyl. Also, the halogenated alkoxy may be that wherein some of the hydrogen atoms are replaced with halogen atoms or all of the hydrogen atoms are replaced with halogen atoms. The halogenated alkyl and halogenated alkoxy have 1 to 6, preferably 1 to 4 carbon atoms.

Examples of the alkyl in alkylsulfonyl and alkylsulfinyl include those exemplified for $R_1$ to $R_3$, namely, those having 1 to 6, preferably 1 to 4 carbon atoms.

$R_4$ is preferably a hydrogen atom and $R_5$ is preferably cyano, nitro or halogenated alkyl (particularly, trifluoromethyl).

The alkyl and the cycloalkyl represented by $R_6$, $R_7$ and $R_8$ include those exemplified for $R_1$ to $R_3$.

As the aralkyl, preferred are phenyl $C_1$–$C_3$ alkyl such as benzyl, α-phenylethyl, β-phenylethyl and γ-phenylpropyl.

As the aryl, mention may be made of phenyl and naphthyl. These aromatic rings may have the same or different substituents at optional positions. The substituents on the aromatic ring include those mentioned for $R_4$ and $R_5$.

The pyridyl includes 2-pyridyl, 3-pyridyl and 4-pyridyl, which may have the substituents mentioned above for $R_4$ and $R_5$.

The alkylene represented by A includes straight- or branched ones having 2 to 4 carbon atoms, which may be ethylene, trimethylene, tetramethylene and 1,2-dimethylethylene.

The aryl and the pyridyl represented by Ar include those exemplified for $R_6$, $R_7$ and $R_8$ and may have the same substituents.

The ring represented by

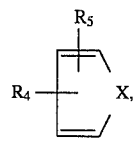

which is the 4-position substituent of dihydropyridine, means a benzene ring when X is vinylene (—CH=CH—); and pyridine when X is azomethine (—CH=N—). The ring may bind to the 4-position of the dihydropyridine at an optional position.

The substituents $R_4$ and $R_5$ may be at any position of ortho-, meta- and para-positions relative to the carbon atom binding to the 4-position of the dihydropyridine, with preference given to the ortho- and/or meta-position(s).

The dihydropyridine derivative (I) and acid addition salts thereof are exemplified by the compounds and acid addition salts thereof shown in Table 1.

TABLE 1

| $R_1$ | $R_2$ | $R_3$ | $R_4$ | $R_5$ | X | A | Ar | $R_8$ | n |
|---|---|---|---|---|---|---|---|---|---|
| 1 Me | Me | Me | H | $NO_2$ | vinylene | ethylene | phenyl | phenyl | 1 |
| 2 Me | Me | Me | H | $NO_2$ | vinylene | ethylene | p-fluorophenyl | phenyl | 1 |
| 3 Me | Me | Me | H | $NO_2$ | vinylene | trimethylene | phenyl | phenyl | 1 |
| 4 Me | Me | Me | H | CN | azomethine | ethylene | phenyl | phenyl | 1 |
| 5 Me | Me | Me | H | $CF_3$ | azomethine | ethylene | phenyl | phenyl | 1 |

Note: Me means methyl.

Preferred dihydropyridine derivatives (I) and acid addition salts thereof are 2-[p-(4-benzhydrylpiperazino)phenyl]ethyl methyl 2,6-dimethyl-4-(3-nitrophenyl)-1,4-dihydropyridine-3,5-dicarboxylate, 2-[p-(4-benzhydrylpiperazino)phenyl]ethyl methyl 2,6-dimethyl-4-(4-cyano-2-pyridyl)-1,4-dihydropyridine-3,5-dicarboxylate, and acid addition salts thereof.

The dihydropyridine derivative (I) can be produced by subjecting an optional portion constituting said dihydropyridine derivative (I) and the residual portion to a step known per se, particularly dehydrating ring closure reaction.

Specific methods for the production are shown in Japanese Patent Unexamined Publication No. 107975/1988 (U.S. Pat. No. 4,849,429), Japanese Patent Unexamined Publication No. 112560/1988 (U.S. Pat. No. 4,910,195), Japanese Patent Unexamined Publication No. 225356/1988 (U.S. Pat. No. 488,619, EP-A-257616), Japanese Patent Unexamined Publication No. 201765/1983 (U.S. Pat. No. 4,892,875), Japanese Patent Unexamined Publication No. 99042/1988 (U.S. Pat. No. 4,886,819, EP-A-257616), Japanese Patent Unexamined Publication No. 152351/1988 (U.S. Pat. No. 4,910,195) and Japanese Patent Unexamined Publication No. 260064/1986.

The dihydropyridine derivative (I) thus produced can be subjected to known separation and purification steps, such as concentration, extraction, chromatography, reprecipitation and recrystallization, as necessary, to provide same at an optional purity.

Since the dihydropyridine derivative (I) has a basic group, it can be converted to an acid addition salt by a known method. The salt is subject to no particular limitation as long as it is pharmacologically acceptable. Examples of the salt include salts with inorganic acid, such as hydrochloride, hydrobromide, phosphate and sulfate; and salts with organic acid, such as acetate, succinate, maleate, fumarate, malate and tartrate.

The dihydropyridine derivatives (I) and acid addition salts thereof, which are the active ingredients in the present invention, are useful for the prevention and treatment of diseases on which $PGI_2$ acts effectively. The dihydropyridine derivatives (I) and acid addition salts thereof promote production of $PGI_2$ in vascular endothelial cells of mammals, thereby allowing the actions of $PGI_2$, such as vasodilating action, bronchodilating action, gastric acid secretion-suppressive action and tumor metastasis-suppressive action, to be exerted. Accordingly, they are expected to be useful in preventing and/or treating hypertension, bronchial asthma and gastric ulcer, as well as suppressing tumor metastasis. In addition, these compounds are useful for the prevention and/or treatment of various diseases caused by the lack or shortage of $PGI_2$, such as arteriosclerosis, heart failure and thrombus. Moreover, promotion of $PGI_2$ production results in organ blood flow-increasing action by $PGI_2$, which in turn renders these compounds useful for the prevention and/or treatment of organ circulatory disorders such as nephropathy (e.g., nephrosis syndrome, glomerulonephritis and diabetic nephropathy).

The dihydropyridine derivatives (I) and acid addition salts thereof suppress increase of lipids in blood and are useful for the prevention and/or treatment of hyperlipemia and improvement of lipid metabolism in mammals. They are also useful for the prevention and/or treatment of arteriosclerosis caused by hyperlipemia.

The dihydropyridine derivatives (I) and acid addition salts thereof are useful for the prevention and/or treatment of cerebral diseases in mammals, such as cerebral stroke, cerebral edema, cerebral softening, cerebral hemorrhage and cerebral infarction.

Examples of the mammals include mouse, rat, rabbit, dog, cat and human.

The dihydropyridine derivatives (I) and acid addition salts thereof are extremely low toxic and highly safe.

When the dihydropyridine derivative (I) or an acid addition salt thereof is used as a pharmaceutical mentioned above, pharmacologically acceptable additives, such as carrier, excipient and diluent, are mixed as appropriate with pharmaceutically required ingredients, and prepared into pharmaceutical compositions in the form of powders, granules, tablets, capsules, syrups or injections, which can be administered orally or parenterally.

The dihydropyridine derivative (I) or an acid addition salt thereof is contained in the above-mentioned pharmaceutical composition in its effective amount. While the dose varies depending on administration route, symptom, body weight and age of patients, the dihydropyridine derivative (I) or an acid addition salt thereof is preferably administered in an amount of 0.1–100 mg/human/day, preferably 1–20 mg/human/day in one to several times divided doses a day when administering to an adult patient. In the case of intravenous administration, the dihydropyridine derivative (I) or an acid addition salt thereof is preferably administered in an amount of 0.1 to 300, preferably 5 to 100 μg/human/day in one to several times divided doses a day.

The present invention is described in more detail in the following by illustrative experimental examples, examples and reference examples, to which the invention is not limited.

As regards $^1$H-NMR, used was $CDCl_3$ unless otherwise

EXPERIMENTAL EXAMPLE 1

Promotion of $PGI_2$ Production

An experiment with regard to the promotion of $PGI_2$ production by the dihydropyridine derivatives (I) and acid addition salts thereof was performed as in the following. The results are shown in Table 2.
(1) Cells Vascular endothelial cells isolated from the artery of 6 weeks old rats.
(2) Medium Culture medium was D-MEM medium supplemented with FCS (final concentration 3%), heparin (final concentration 5 IU/ml), ECGF (endovascular cell growth factor, final concentration 50 μg/ml), penicillin (final concentration 100 IU/ml) and streptomycin (final concentration 100 μg/ml).

Assay medium was OpTi-MEM medium supplemented with BSA (final concentration 0.01%), heparin (final concentration 5 IU/ml), ECGF (final concentration 50 μg/ml), penicillin (final concentration 100 IU/ml) and streptomycin (final concentration 100 μg/ml).
(3) Culture vessel Collagen-coated 10 cm dish and collagen-coated 24 well plate.
(4) Culture Culture of vascular endothelial cells was carried out using a collagen-coated dish. The culture conditions were temperature of 37° C. in 95% air-5% $CO_2$. Subculture was done by a conventional method using trypsin/ethylene diaminetetraacetic acid solution (split ratio=1:2). Prior to the experiment, the cells were inoculated in a collagen-coated 24 well plate at $1\times10^4$ cells/well and cultured for 7 days in a culture medium. Then, the medium was changed to an assay medium and the cells were preincubated for 2 hours. The medium was replaced with an assay medium supplemented with a test drug and the cells were cultured for 1 hour. The culture solution was recovered and stored at −20° C. The cells in each well were counted.
(5) Measurement of $PGI_2$ content The $PGI_2$ in each sample was assayed by EIA (enzyme immunoassay) using BIOTRAK 6-keto-$PGI_1\alpha$EIA System (Amersham).
(6) Test drug Used were the compound of the present invention (Compound 2 to be noted below, dissolved in dimethyl sulfoxide), nicardipine (dissolved in dimethyl sulfoxide) and human thrombin.

TABLE 2

| Drug | Amount added | $PGI_2$ content (pg/$10^4$ cells) |
|---|---|---|
| Compound 2 | $10^{-6}$M | 101 ± 22 |
| | $10^{-7}$M | 79 ± 7 |
| | $10^{-8}$M | 50 ± 3 |
| Compound 2 + thrombin | $10^{-8}$M 1 IU/ml | 98 ± 7 |
| Thrombin | 1 IU/ml | 71 ± 9 |
| Nicardipine | $10^{-6}$M | 40 ± 18 |
| not used | — | 32 ± 16 |

Note: sample number = 4

As the results of Experimental Example 1 show, the compound of the present invention has a $PGI_2$ production-promoting action and exhibits action and effects equal to or greater than those of thrombin, a known $PGI_2$ production-promoter. It is also known that nicardipine, which is structurally analogous to the dihydropyridine derivative (I) of the present invention, does not have a $PGI_2$ production-promoting action.

The effects of the dihydropyridine derivative (I) and an acid addition salt thereof against hyperlipemia and arteriosclerosis were examined by the following Experimental Examples 2–4.

EXPERIMENTAL EXAMPLE 2

A high cholesterol diet [normal diet (trademark CE-2) added with 2% cholesterol, 1% cholic acid and 5% linoleic acid, manufactured by Japan Clare Corp.] was fed to male C57BL/6Cr mice (weighing about 20 g) and a test drug dissolved in 1% Tween 80 was orally administered in a predetermined dose to the mice once a day for 9 weeks. The dose contained 10 mg/kg body weight of the compound of the present invention (Compound 2 to be noted below), or a comparison drug of nilvadipine (10 mg/kg body weight) or clofibrate (100 mg/kg body weight). At 9 weeks, the amount of various lipids in the serum was measured using a measurement kit manufactured by Wako Pure Chemicals Co., Ltd. The results are shown in Table 3.

TABLE 3

| | Drug | n | HDL mg/dl | Free cholesterol (mg/dl) | Triglyceride (mg/dl) |
|---|---|---|---|---|---|
| Normal diet | none | 10 | 47 ± 2 | 7 ± 2 | 98 ± 4 |
| High cholesterol diet | none | 3 | 18 ± 6 | 85 ± 50 | 56 ± 11 |
| | vehicle | 8 | 11 ± 2 | 60 ± 10 | 66 ± 5 |
| | Compound 2 | 9 | 43 ± 6 | 36 ± 5 | 97 ± 11 |
| | nilvadipine | 10 | 28 ± 3 | 39 ± 6 | 90 ± 7 |
| | clofibrate | 10 | 57 ± 6 | 33 ± 2 | 115 ± 7 |

The group fed with a high cholesterol diet but was not administered with a drug, and the group administered with a vehicle alone showed increase in free cholesterol and decrease in HDL and triglyceride. HDL has an action of removing cholesterol. Therefore, a decrease thereof causes an increase of cholesterol. The group administered with the compound of the present invention suppressed increase in cholesterol, and HDL and triglyceride values were approximately the same as those of the group fed with a normal diet.

EXPERIMENTAL EXAMPLE 3

A high cholesterol diet [normal diet (trademark CR-3) added with 2% cholesterol and 1% cholic acid, manufactured by Japan Clare Corp.] was fed to male New zeal albino rabbits (weighing about 2 kg), and a test drug dissolved in 1% Tween 80 was orally administered to the rabbits once a day for 5 weeks in a predetermined dose. The dose contained 10 mg/kg body weight of the compound of the present invention (Compound 2 to be mentioned below), and a comparison drug of nilvadipine (10 mg/kg body weight) or clofibrate (100 mg/kg body weight). At 5 weeks, the amount of various lipids in the serum was measured. Total cholesterol, triglyceride and phospholipid were determined by the enzyme method. The lipoprotein fraction in the serum was determined by heparin-Ca nephelometry. The results are shown in Table 4.

(1) Measurement of lipid amount

The artery was removed under $CO_2$ inhalation. The abdominal artery (5 cm) was removed from the renal artery and placed in a mixed solution (5 ml) of chloroform:methanol=2:1. The artery was left standing at 50° C. for 30 minutes to allow liberation of lipids in the artery. The lipid amount in the supernatant was measured using a measurement kit manufactured by Wako Pure Chemical Industries, Ltd.

(2) Measurement of Ca content

The residue obtained by the above step was placed in a mixed solution (1 ml) of nitric acid:sulfuric acid: perhydrochloric acid:water=1:1:4:1 and completely dissolved. The Ca concentration in the solution was measured using a measurement kit manufactured by Wako Pure Chemical Industries, Ltd.

(3) Measurement of arteriosclerosis area

TABLE 4

| | Drug | n | Total cholesterol (mg/dl) | LDL (mg/dl) | VLDL (mg/dl) | Triglyceride (mg/dl) | phospholipid (mg/dl) |
|---|---|---|---|---|---|---|---|
| Normal diet | none | 6 | 42 ± 2 | 101 ± 18 | 71 ± 20 | 60 ± 11 | 98 ± 6 |
| High cholesterol diet | vehicle | 9 | 3276 ± 248 | 5344 ± 768 | 6372 ± 772 | 279 ± 46 | 986 ± 55 |
| | Compound 2 | 5 | 2630 ± 352 | 3612 ± 597 | 4552 ± 512 | 225 ± 48 | 843 ± 55 |
| | nirdipine | 6 | 3022 ± 146 | 4602 ± 681 | 5840 ± 311 | 280 ± 69 | 1003 ± 42 |
| | clofibrate | 5 | 2663 ± 216 | 3540 ± 453 | 5052 ± 979 | 376 ± 86 | 955 ± 50 |

The group administered with the compound of the present invention exhibited decrease in total cholesterol, LDL, VLDL, triglyceride and phospholipid, as compared with the group administered with a vehicle alone. The action of the compound of the present invention was approximately equal to or greater than that of a known therapeutic agent for hyperlipemia, clofibrate.

EXPERIMENTAL EXAMPLE 4

A high cholesterol diet [normal diet (trademark CR-3) added with 2% cholesterol and 1% cholic acid, manufactured by Japan Clare Corp.] was fed to male New zeal albino rabbits (weighing about 2 kg), and a test drug dissolved in 1% Tween 80 was orally administered to the rabbits once a day for 7 weeks in a predetermined dose. The dose contained 10 mg/kg body weight of the compound of the present invention (Compound 2 to be mentioned below), or a comparison drug of nilvadipine (10 mg/kg body weight) or clofibrate (100 mg/kg body weight). At 7 weeks, the artery was removed, and the amount of various lipids in the artery, Ca content and arteriosclerosis area were determined. The results are shown in Table 5. The measurement methods were as follows.

The thoracic aorta (ca. 10 cm) was removed from the aortic arch, and tissues thereof were subjected to Sudan II fat staining. The arteriosclerosis area was determined by an image analyzer. The arteriosclerosis area was expressed in percentage to the total area of the aorta.

TABLE 5

| | Drug | n | Total cholesterol (mg/g) | Free cholesterol (mg/g) | Esterified cholesterol (mg/g) | Ca content (mg/g) | Arteriosclerosis area (%) |
|---|---|---|---|---|---|---|---|
| Normal diet | none | 6 | 5.9 ± 0.3 | 1.9 ± 0.3 | 4.0 ± 0.4 | 0.17 ± 0.04 | 0 ± 0 |
| High cholesterol diet | vehicle | 6 | 12.0 ± 1.8 | 4.6 ± 0.6 | 7.4 ± 1.5 | 0.69 ± 0.37 | 78 ± 6 |
| | Compound 2 | 5 | 8.0 ± 1.1 | 4.1 ± 0.8 | 3.9 ± 0.7 | 0.11 ± 0.01 | 42 ± 11 |
| | nirdipine | 4 | 12.5 ± 1.7 | 4.5 ± 0.8 | 8.0 ± 1.0 | 0.20 ± 0.06 | 67 ± 8 |
| | clofibrate | 4 | 12.9 ± 2.5 | 5.4 ± 1.3 | 7.5 ± 1.8 | 0.59 ± 0.29 | 79 ± 11 |

The group administered with the compound of the present invention exhibited decrease in total cholesterol, free cholesterol, esterified cholesterol and Ca content, as well as suppression of arteriosclerosis, in comparison with the group administered with a vehicle alone. The action of the compound of the present invention was approximately equal to or greater than that of a known therapeutic agent for hyperlipemia, clofibrate.

From the results of Experimental Examples 2–4, it is evident that the dihydropyridine derivative (I) and an acid addition salt thereof suppress increase in lipids in blood, particularly, cholesterol, LDL and VLDL, which cause problems with regard to hyperlipemia, and are useful as therapeutic agents for hyperlipemia. In addition, they decrease lipid amount in blood and are useful for the prevention and treatment of arteriosclerosis.

The effects of the dihydropyridine derivative (I) and an acid addition salt thereof against cerebral diseases were examined in the following Experimental Examples 5–8.

EXPERIMENTAL EXAMPLE 5

Suppression of Incidence of Cerebral Stroke

Test drugs

Compound 2 (compound of the present invention) to be mentioned below and benidipine (control drug).

Test method

Male SHRSP (Stroke-Prone Spontaneously Hypertensive Rats, 10 weeks old) were housed in individual cages and bred until 12 weeks old on an SP feed (manufactured by Funabashi Farm, hereinafter the same). At 13 weeks of age, the feed was changed to an SP feed containing 4% NaCl, and the rats were bred thereafter on the same feed. The drug administration was started from 14 weeks of age and continued for 8 weeks. The test drug or a vehicle was orally administered daily by 10 ml/kg and the rats were grouped into a group administered with 0.3 mg/kg/day, 1 mg/kg/day or 3 mg/kg/day of the test drug. The systolic blood pressure was measured every week using a programmable sphygmonanometer (PS-200A, manufactured by Riken Kaihatsu Corp.) before and 2 hours after the drug administration. The day of the incidence of cerebral stroke and the date of death, when it happened, were recorded. The brain, heart and kidney were removed and visually observed for the possible cerebral hemorrhage or cerebral softening, and immobilized with 10% formalin-phosphate buffer (pH 7.4). The animals which survived through the experiment were refluximmobilized with 250 ml of 4% formalin-phosphate buffer (pH 7.4) and the above-mentioned organs were removed. Using the same solution, post-immobilization was performed at 4° C.

Results

The survival ratio of each group and possible damage to the removed brain are shown in the following Table 6.

TABLE 6

Visual observation of brain damage in SHRSP

| | | Test drug | | | | | |
|---|---|---|---|---|---|---|---|
| | | Compound 2 | | | Benidipine | | |
| | | Dose (mg/kg) | | | | | |
| | Vehicle | 0.3 | 1 | 3 | 0.3 | 1 | 3 |
| Survival ratio | 0/9 | 0/9 | 9/9 | 9/9 | 0/9 | 5/9 | 8/9 |
| Average survival days* (maximum 57 days) | 27 ± 5 | 34 ± 5 | 57 ± 0 | 57 ± 0 | 28 ± 4 | 48 ± 5 | 55 ± 2 |
| Incidence of stroke | 7/9 | 6/9 | 1/9 | 0/9 | 6/9 | 7/9 | 3/9 |
| Hemorrhage | 6/9 | 5/9 | 1/9 | 0/9 | 2/9 | 7/9 | 3/9 |
| Edema or softening | 4/9 | 3/9 | 1/9 | 0/9 | 4/9 | 6/9 | 0/9 |

TABLE 6-continued

Visual observation of brain damage in SHRSP

| | | Test drug | | | | | |
|---|---|---|---|---|---|---|---|
| | | Compound 2 | | | Benidipine | | |
| | | Dose (mg/kg) | | | | | |
| | Vehicle | 0.3 | 1 | 3 | 0.3 | 1 | 3 |

Number of positive animals/total animals
*: mean ± SE

1. Survival ratio

A death case was found in the group (control) administered with a vehicle (control group) from 2 weeks after the initiation of the experiment and the average survival days were 27± 5. In contrast, the group administered with 0.3 mg/kg/day of Compound 2 of the present invention showed somewhat prolonged survival days and the average survival days were 34±5. All animals administered with 1 mg/kg/day or 3 mg/kg/day of the compound of the present invention survived through the experiment.

2. Visual observation of brain

In the vehicle group, 7 out of 9 animals had hemorrhage, edema or cerebral softening. In contrast, 5 out of 9 animals administered with 0.3 mg/kg/day of Compound 2 of the present invention had cerebral stroke. However, when Compound 2 was administered by 1 mg/kg/day, only one out of 9 animals suffered from brain damage and when it was administered by 3 mg/kg/day, incidence of cerebral stroke was not found.

Summary

From the aforementioned results, it is evident that administration of Compound 2 of the present invention by 1 mg/kg/day or more to SHRSP suffering from severe hypertension induced by NaCl load results in the notable suppression of the incidence of cerebral stroke and the death caused thereby. The group administered with 1 mg/kg/day of Compound 2 of the present invention showed the incidence of cerebral stroke only in one case out of 9, even though they showed an average systolic blood pressure of 250 mmHg or more from 3 weeks after the initiation of the experiment, which reached 270 mmHg when the experiment ended. In contrast, the control drug, benidipine, showed weaker suppression of the incidence of cerebral stroke in SHRSP than did Compound 2 of the present invention.

EXPERIMENTAL EXAMPLE 6

Suppression of Incidence of Cerebral Stroke

Test drugs

Compound 2 (compound of the invention) to be mentioned below, nicardipine and hydralazine (both being control drugs).

Test method

The test was done according to Experimental Example 5 above, except that the test period was set for 12 weeks.

Results

The survival ratio (12 weeks after the administration) is summarized in the following Table 7.

TABLE 7

Survival ratio of SHRSP administered with various drugs

| Test drug | Dose (mg/kg body weight) | Survival ratio |
|---|---|---|
| Vehicle |  | 0/10 |
| Compound 2 | 0.3 | 0/10 |
| Compound 2 | 1 | 10/10 |
| Compound 2 | 3 | 10/10 |
| Nicardipine | 3 | 0/10 |
| Hydralazine | 10 | 5/10 |
| Nicardipine | 10 | 5/10 |

Number of positive animal/total number of animals

1. Survival ratio

The group administered with a vehicle (control group) showed emergence of cerebral stroke symptoms, such as piloerection and paralysis, from 2 weeks after the initiation of the test and all animals died in 37 days. Fifty percent of the animals died in 29 days ($D_{50}$) in this control group. In contrast, the group administered with 0.3 mg/kg/day of Compound 2 of the present invention showed the symptoms of cerebral stroke from about 3 weeks after the initiation of the test, and all animals died in 68 days from the NaCl load application. The $D_{50}$ of this group was 37 days, showing somewhat prolonged survival period as compared with the control group. When Compound 2 of the present invention was administered by 1 mg/kg/day or 3 mg/kg/day, no animal developed the symptom of cerebral stroke during 12 weeks of administration, and all animals survived through the test. In the group administered with 3 mg/kg/day of nicardipine, however, cerebral stroke was developed two weeks thereafter and all animals died in 50 days. The $D_{50}$ of this group was 35 days. The group administered with nicardipine (10 mg/kg/day) and the group administered with hydralazine (10 mg/kg/day) showed the incidence of cerebral stroke in some of the rats from 3 weeks after the NaCl load application. However, one-half of the rats survived until even 12 weeks later ($D_{50}$ was 68 days and 78 days, respectively), and the evident life-prolonging effect, which is considered to be due to the suppression of the incidence of cerebral stroke, was found.

2. Visual observation of brain

The brain of the rats that survived 12 weeks of administration was removed and visually observed. Only one animal from the group administered with Compound 2 by 1 mg/kg/day showed manifestation of cerebral softening and there was found no other abnormality. In the group administered with Compound 2 by 3 mg/kg/day, no manifestation of cerebral softening or cerebral hemorrhage was found. In contrast, the group administered with 10 mg/kg/day of nicardipine showed evident bilateral cerebral softening in 4 cases out of 5 and the group administered with 10 mg/kg/day of hydralazine showed cerebral softening in one case out of five. In appearance, however, no animal showed an indication of cerebral hemorrhage.

Summary

From the foregoing results, it is evident that administration of Compound 2 of the present invention by 1 mg/kg or more results in complete suppression of the symptoms of cerebral stroke, thereby keeping all animals alive.

Moreover, it was found that consecutive oral administration of 10 mg/kg of nicardipine or hydralazine suppressed the incidence of cerebral stroke. Since administration of hydralazine resulted in evident maintenance of low blood pressure, suppression of the incidence of cerebral stroke by hydralazine was considered to be ascribed to the hypotensive action of this drug. On the other hand, 5 out of 10 animals administered with a high dose of nicardipine survived. However, 4 out of the 5 had evident bilateral cerebral softening. Accordingly, nicardipine is considered to prevent cerebral stroke and increase survival ratio, whereas its action is clearly weaker than that of Compound 2 of the present invention.

EXPERIMENTAL EXAMPLE 7

Treatment of Rats with Cerebral Stroke

Test drug

Compound 2 (compound of the present invention) to be mentioned below, nicardipine and hydralazine (both being control drugs).

Test method

SHRSP (9 weeks old) were bred on a 4% NaCl-containing SP feed and the animals, as to which the incidence of cerebral stroke was confirmed on the basis of the change in appearance, weight loss and neurological symptoms, were selected. The animals were housed in individual cages from the initiation of the experiment and they were bred on an SP feed thereafter. The test drug or a vehicle was forcibly administered orally for 21 consecutive days in the dose of 10 ml/kg. The appearance, general conditions and development of neurological symptoms were examined and evaluated on a predetermined date and time according to the following score, and survival ratio was checked alongside. With regard to the death case, the brain of the animal was removed, visually observed for possible cerebral hemorrhage and cerebral softening, and immobilized with 10% formalin.

Condition evaluation score 1) motor ataxia
   no abnormality: 0, light disorder: 1, severe disorder: 2
2) abnormal posture
   no abnormality: 0, light disorder: 1, severe disorder: 2
3) righting reflex
   observed: 0, not observed: 1
4) flexion reflex of hindlimb
   observed: 0, not observed: 1
5) confirmation of visual location
   no abnormality: 0, light disorder: 1, severe disorder: 2
6) grip strength (under tail suspension)
   no abnormality: 0, light loss: 1, severe loss: 2
7) suppleness (by touching)
   no abnormality: 0, light sclerosis: 1, severe sclerosis: 2
8) diarrhea observed: 0, not observed: 1

Since severe symptoms gain points in all evaluation items and reach extremely big scores, the maximum score obtainable for an animal having severe symptoms was set for 5 and the animals exceeding 5 in the score are also expressed by 5. The death case was calculated as scoring 6.

Results

1. General conditions and neurological symptoms

The scores of respective groups are shown in Table 8.

TABLE 8

Effects of Compound 2 on neurological score of SHRSP having cerebral stroke

| Test drug | Dose (mg/kg) | Test animal (n) | Initiation of test | Administered days | | |
|---|---|---|---|---|---|---|
| | | | | 7 days | 14 days | 21 days |
| Vehicle | | 12 | 2.8 ± 1.4 | 3.8 ± 1.7 | 4.6 ± 1.7 | 4.6 ± 1.6 |
| Compound 2 | 1 | 9 | 2.9 ± 1.2 | 0.7 ± 0.8[2] | 0.3 ± 0.5[3] | 0.3 ± 0.5[3] |
| Compound 2 | 3 | 8 | 2.9 ± 1.5 | 0.4 ± 0.5[2] | 0.0 ± 0.0[3] | 0.0 ± 0.0[3] |
| Nicardipine | 10 | 7 | 2.7 ± 1.4 | 2.0 ± 2.4 | 2.0 ± 2.6 | 1.9 ± 2.9[1] |
| Hydralazine | 10 | 7 | 2.3 ± 1.4 | 1.6 ± 1.7[1] | 1.1 ± 1.6[2] | 2.1 ± 2.5 |

Mean ± SD
[1]: $P < 0.05$
[2]: $P < 0.01$
[3]: $P < 0.001$ (significant difference from animals administered with vehicle according to Willcoxon test)

The symptom score of the respective groups at the initiation of the experiment was 2.3–2.9, showing not much difference between the groups. The symptom score worsened every week in the vehicle group and it reached 4.6 after day 14. The group administered with Compound 2 of the present invention showed significant improving effect, as compared with the vehicle group, after day 7 from the initiation of the experiment in the groups administered with either dose. In particular, the high dose group (3 mg/kg/day) showed the score 0 in all animals after day 14, indicating recovery to the normal state. The group administered with a control drug, i.e., nicardipine (10 mg/kg/day) or hydralazine (10 mg/kg/day), showed improvement of symptoms, though weaker than that of Compound 2 of the present invention.

2. Survival ratio

The survival ratio of each group and possible damage of the removed brain are shown in Table 9.

TABLE 9

Brain damage in SHRSP

| | | Test drug | | | |
|---|---|---|---|---|---|
| | | Compound 2 | | Nicardipine | Hydralazine |
| | | Dose (mg/kg) | | | |
| | Vehicle | 1 | 3 | 10 | 10 |
| Survival ratio | 5/12 | 9/9 | 8/8 | 5/7 | 5/7 |
| Incidence of stroke | 11/12 | 8/9 | 7/8 | 6/7 | 6/7 |
| Hemorrhage | 10/12 | 5/9 | 6/8 | 6/7 | 5/7 |
| Edema or softening | 11/12 | 5/9 | 1/8 | 5/7 | 5/7 |

Number of positive animal/total number of animals

A death case was found in the vehicle group from about 7 days after the initiation of the experiment, and the survival ratio of the animals was 42% when the experiment ended. In contrast, the animals of the groups administered with either dose of Compound 2 of the present invention all survived. The groups administered with control drugs, i.e., nicardipine (10 mg/kg/day) or hydralazine (10 mg/kg/day), showed 2 death cases out of 7 and the survival ratio was 71%.

3. Pathological observation of brain (visual)

The brain of the animals was removed either after the completion of the experiment or when the animal died, and development of cerebral hemorrhage or cerebral edema was visually examined. In the vehicle group, 11 out of 12 showed hemorrhage, edema or softening. In the groups administered with Compound 2 of the present invention in the dose of 1 mg/kg/day or 3 mg/kg/day, a trace mainly of cerebral hemorrhage was found in 8 out of 9 and 7 out of 8, respectively. However, edema and softening were dose-dependently suppressed. The groups administered with nicardipine or hydralazine had cerebral lesion in 6 cases out of 7 in both groups, and the manifestation of edema and softening was highly frequent, as compared with Compound 2 of the present invention.

4. Pathological observation (visual) of brain from animals survived till the end The brain of the 5 animals survived in the vehicle group was markedly swollen and deviation toward the opposite side of the brain was observed. In addition, hemorrhage lesion or trace thereof was found in all 5 cases. The animals administered with Compound 2 of the present invention (either dose) showed only trace of hemorrhage, and swelling of the brain was not found. On the other hand, all animals administered with nicardipine or hydralazine and survived showed trace of cerebral hemorrhage. Also, deviation toward the opposite side of the brain, which was caused by swelling, was also found in some cases.

Summary

From the foregoing results, it is evident that Compound 2 of the present invention notably improved the survival ratio and neurological symptoms of SHRSP with cerebral stroke, and suppressed the progress into cerebral edema or cerebral softening. In contrast, while the groups administered with nicardipine or hydralazine showed a tendency to have an improved survival ratio and neurological symptoms, suppression of the aggravation of cerebral lesion was extremely weaker than Compound 2 of the present invention.

EXPERIMENTAL EXAMPLE 8

Tissue Observation/Treatment of Rats with Cerebral Stroke

Test drug

Compound 2 (compound of the present invention) to be mentioned below, nicardipine and hydralazine (both being control drugs).

Test method

SHRSP (7 weeks old) were housed in individual cages and bred on an SP feed. At 9 weeks of age, the feed was changed to an SP feed containing 4% NaCl. After confirming the emergence of the symptoms of cerebral stroke, the feed was changed back to the SP feed for breeding the rats. A test drug or a vehicle was administered in the same manner as in Experimental Example 2 and the brain of the animals survived to the last was removed and used as a sample. Each sample was immobilized with a 10% neutral buffer formalin solution, and dehydrated, cleared and embedded with paraffin by conventional methods. A specimen of 3 μm thickness was prepared and subjected to HE staining, PAS staining and EGV staining in order, and histopathologically observed with an optical microscope. Cerebral hemorrhage, which is one of the causes of cerebral stroke, and possible necrosis of surrounding tissues, edema and cystic lesion were used an indices of the therapeutic effect.

Results (1) Vehicle group

Severe cerebral hemorrhage or a symptom caused thereby was found in all five cases.

(2) Group administered with 1 mg/kg/day of Compound 2 of the present invention

Medium degree hemorrhage or a symptom caused thereby was found in two cases out of five. In one case, only a trace of cerebral hemorrhage lesion was found and no symptom was found in the other two cases.

(3) Group administered with 3 mg/kg/day of Compound 2 of the present invention

A light degree symptom caused by cerebral hemorrhage was found in one case out of five. In the remaining four cases, only a trace of cerebral hemorrhage lesion was found.

(4) Group administered with 10 mg/kg/day of nicardipine

Severe cerebral hemorrhage or a symptom caused thereby was found in four cases out of five. No symptom was found in the remaining one case.

(5) Group administered with 10 mg/kg/day of hydralazine

A medium degree symptom caused by cerebral hemorrhage was found in two cases out of three. No symptom was found in the remaining one case.

The results are summarized in the following Tables 10 and 11.

TABLE 10

Degree of cerebral hemorrhage or accompanied symptoms in respective drug group

| Drug | Degree of cerebral hemorrhage or accompanied symptom | | | | |
|---|---|---|---|---|---|
| | maximum | medium | light | trace | none |
| Vehicle | 5 | | | | |
| Compound 2 1 mg/kg | | 2 | | 1 | 2 |
| Compound 2 3 mg/kg | | | 1 | 4 | |
| Nicardipine 10 mg/kg | 4 | | | | 1 |
| Hydralazine 10 mg/kg | | 2 | | | 1 |

TABLE 11

Possible new cerebral hemorrhage lesion in respective drug groups

| Drug | New cerebral hemorrhage lesion | |
|---|---|---|
| | present | none |
| Vehicle | 4 | 1 |
| Compound 2 1 mg/kg | | 5 |
| Compound 2 3 mg/kg | | 5 |
| Nicardipine 10 mg/kg | 2 | 3 |
| Hydralazine 10 mg/kg | | 3 |

Summary

The therapeutic effect of Compound 2 of the present invention on SHRSP with cerebral stroke was histopathologically examined. As a result, maximum degree cerebral hemorrhage or a symptom caused thereby was found in all five cases of the vehicle group, whereas only a medium degree symptom caused by cerebral hemorrhage was found in two cases out of five of the group administered with 1 mg/kg/day of Compound 2 of the present invention, and only a light degree symptom caused by cerebral hemorrhage was found in one case out of five of the group administered with 3 mg/kg/day of Compound 2 of the present invention. Moreover, a new hemorrhage lesion, which was considered to be developed after the administration of the drug, was not found in the groups administered with Compound 2 (both doses) of the present invention.

Based on the above results, it is evident that Compound 2 of the present invention dose-dependently suppressed necrosis of surrounding tissues, edema and the progress of cystic lesion, which are caused by cerebral hemorrhage, as well as suppressed the development of new cerebral hemorrhage. While the group administered with the control drug, hydralazine (10 mg/kg/day), showed the same degree of effects as was achieved by the administration of 1 mg/kg/day of Compound 2 of the present invention, the group administered with nicardipine (10 mg/kg/day) scarcely showed effects.

REFERENCE EXAMPLE 1

Synthesis of 2-[p-(4-benzhydrylpiperazino)phenyl]ethyl methyl 2,6-dimethyl-4-(3-nitrophenyl)-1,4-dihydropyridine-3,5-dicarboxylate (Compound 1) and hydrochloride thereof (Compound 2):

3-Nitrobenzaldehyde (1.144 g, 7.57 mmol), [p-(4-benzhydrylpiperazino)phenyl]ethyl acetoacetate (3.464 g, 7.59 mmol) and methyl 3-aminocrotonate (873 mg, 7.58 mmol) were charged in a 100 ml-eggplant type flask. Isopropanol (12 ml) was added thereto. The flask was equipped with a Dimroth condenser and refluxed under heating for 16 hours. The reaction solvent was distilled away under reduced pressure and the residue was separated by column chromatography [silica gel, chloroform—methanol (45:1)] and column chromatography [silica gel, ethyl acetate—n-hexane (2:3)], and the crude product obtained was purified by high performance liquid chromatography to give 2.503 g of the title Compound 1 (yield 48%).

$IR\nu_{max}^{KBr}$ cm$^{-1}$: 1680, 1520

$^1$H-NMR δ:

8.06 (1H, t, J=2 Hz), 7.97 (1H, ddd, J=8; 2; 1 Hz), 7.1–7.6 (12H), 7.03 (2H, d, J=8.6 Hz), 6.80 (2H, d, J=8.6 Hz), 6.02 (1H, s), 5.07 (1H, s), 4.26 (1H, s), 4.22 (2H, t, J=7 Hz), 3.64 (3H, s), 3.15 (4H, dd, J=5; 4.7 Hz), 2.81 (2H, t, J=7 Hz), 2.55 (4H, dd, J=5; 4.7 Hz), 2.33, 2.28 (3H, s, respectively)

The Compound 1 (2.124 g, 3.16 mmol) was placed in a 200 ml—eggplant type flask and the flask was rubber-sealed. Methylene chloride (100 ml) was added thereto, and after dissolution of the content, the mixture was stirred at room temperature for 30 minutes while introducing a hydrogen chloride gas. The resultant crystals were collected by filtration to give about 2.22 g of the title Compound 2.

$IR\nu_{max}^{KBr}$ cm$^{-1}$: 2450, 1680, 1525, 1350

$^1$H-NMR δ:

13.72 (1H, brs), 8.05–7.9 (6H), 7.82, 7.26 (4H, A$_2$B$_2$, q, J=8.6 Hz), 7.6–7.3 (8H), 6.28 (1H, s), 5.2–5.05 (2H), 5.01 (2H, s), 4.27 (2H, t, J=6.5 Hz), 4.3–4.1 (2H), 3.66 (3H, s), 3.65–3.45 (4H), 2.95 (2H, t, J=6.5 Hz), 2.36, 2.33 (3H, s, respectively)

EXAMPLE 1

| Tablets: | |
|---|---|
| (1) Compound 2 | 10 g |
| (2) Fine granule No. 209 for direct compression (Fuji Kagakusha) | 110 g |
|     Magnesium aluminate metasilicate | 20% |
|     Corn starch | 30% |
|     Lactose | 50% |
| (3) Crystalline cellulose | 60 g |
| (4) CMC calcium | 18 g |
| (5) Magnesium stearate | 2 g |

(1), (3) and (4) were passed through a 100 mesh-sieve in advance. (1), (3), (4) and (2) were respectively dried to a certain water content, after which the mixture was kneaded at the above weight ratio by a mixing machine. (5) was added to the homogeneously-mixed powder and was mixed for a short time (30 seconds). The mixed powder was compressed into tablets of 200 mg each.

The tablets may be gastro-coated using a film coating agent such as polyvinyl acetal diethylaminoacetate or coated with a food coloring.

EXAMPLE 2

| Capsules: | |
|---|---|
| (1) Compound 2 | 50 g |
| (2) Lactose | 930 g |
| (3) Magnesium stearate | 20 g |

The above ingredients were weighed and homogeneously mixed, after which the mixed powder was charged in hard gelatin capsules at 200 mg each.

EXAMPLE 3

| Injections: | |
|---|---|
| (1) Compound 2 | 5 mg |
| (2) Glucose | 100 mg |
| (3) Physiological saline | 10 ml |

The mixed solution of the above was filtered through a membrane filter, after which it was sterilized by filtration. The filtrate was aseptically poured into a vial, charged with a nitrogen gas and sealed to afford an intravenous injection.

EXAMPLE 4

Compound 2 (20.1 g) was added to a mixture (1:1,650 g) of unsaturated fatty acid monoglyceride (Excel O-95R, manufactured by Kao Corp.) and polyoxyethylenesorbitan monooleate (TO-10M, manufactured by Nikko Chemical Corp.), and dissolved and stirred at 40° C. to give a non-micell solution. The obtained solution (600 g) and magnesium aluminate metasilicate (370 g, Neusilin $US_2$, manufactured by Fuji Kagaku Sangyo) were nixed in a rotary granulator. Then, Carmellose sodium A (30 g) was mixed and purified water (250 ml) was added for granulation. The granules were dried at 40° C. for 17 hours with a forced-air drier, passed through a 42–200 mesh-sieve to prepare 550 g of granules to be packed in capsules.

What is claimed is:

1. A method for promoting $PGI_2$ production, and for the treatment of hyperlipemia, arteriosclerosis, cerebral edema, cerebral softening or cerebral hemorrhage, comprising administrating an effective amount of the dihydropyridine derivative of the formula (I)

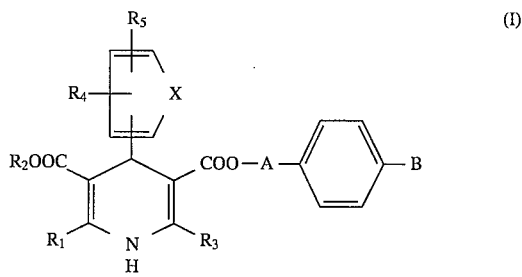

wherein $R_1$, $R_2$ and $R_3$ are the same or different and each is an alkyl, a cycloalkyl or an alkoxyalkyl;

$R_4$ and $R_5$ are the same or different and each is a hydrogen atom, a halogen, nitro, a halogenated alkyl, an alkylsulfonyl, a halogenated alkoxy, an alkylsulfinyl, an alkyl, a cycloalkyl, an alkoxy, cyano, an alkoxycarbonyl or an alkylthio, provided that $R_4$ and $R_5$ are not hydrogen atoms at the same time;

X is a vinylene or an azomethine;

A is an alkylene; and

B is —$N(R_6)(R_7)$ or a group of the formula

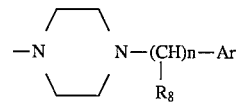

wherein $R_6$, $R_7$ and $R_8$ are the same or different and each is a hydrogen atom, an alkyl, a cycloalkyl, an aralkyl, an aryl or a pyridyl, Ar is an aryl or a pyridyl and n is an integer of 0, 1 or 2; or an acid addition salt thereof.

2. The method of claim 1, wherein $R_1$, $R_2$ and $R_3$ are the same or different and each is an alkyl, $R_4$ is a hydrogen atom, $R_5$ is nitro, a halogenated alkyl or cyano, $R_6$ and $R_7$ are the same or different and each is an alkyl, an aralkyl or an aryl, $R_8$ is an aryl, Ar is an aryl and n is 1.

3. The method of claim 1, which is used for promoting $PGI_2$ production.

4. The method of claim 1, which is used for the treatment of hyperlipemia.

5. The method of claim 1, which is used for the treatment of arteriosclerosis.

6. The method of claim 1, which is used for the treatment of cerebral edema, cerebral softening or cerebral hemorrhage.

* * * * *